US00PP29530P2

(12) United States Plant Patent
Nebelmeir

(10) Patent No.: US PP29,530 P2
(45) Date of Patent: Jul. 17, 2018

(54) ***PORTULACA* PLANT NAMED 'LAZPRT1607'**

(50) Latin Name: ***Portulaca umbraticola* Kunth**
Varietal Denomination: LAZPRT1607

(71) Applicant: Johannes Sebastian Nebelmeir, Marling (IT)

(72) Inventor: Johannes Sebastian Nebelmeir, Marling (IT)

(73) Assignee: Lazzari Societa Agricola a.R.L., Sabaudia (IT)

( * ) Notice: Subject to any disclaimer, the term of this patent is extended or adjusted under 35 U.S.C. 154(b) by 0 days.

(21) Appl. No.: 15/530,402

(22) Filed: Jan. 10, 2017

(51) Int. Cl.
*A01H 5/02* (2018.01)

(52) U.S. Cl.
USPC ..... Plt./471

(58) Field of Classification Search
USPC ..... Plt./471
See application file for complete search history.

*Primary Examiner* — Susan McCormick Ewoldt
(74) *Attorney, Agent, or Firm* — C. A. Whealy

(57) ABSTRACT

A new and distinct cultivar of *Portulaca* plant named 'LAZPRT1607', characterized by its outwardly spreading to creeping growth habit; vigorous growth habit; freely branching habit; freely flowering habit; bright yellow and white-colored flowers; and excellent garden performance.

2 Drawing Sheets

Botanical designation: *Portulaca umbraticola* Kunth.
Cultivar denomination: 'LAZPRT1607'.

BACKGROUND OF THE INVENTION

The present invention relates to a new and distinct cultivar of *Portulaca* plant, botanically known as *Portulaca umbraticola* Kunth, commonly known as Wingpod Purslane, and hereinafter referred to by the name 'LAZPRT1607'.

The new *Portulaca* plant is a product of a planned breeding program conducted by the Inventor in Merano, South Tyrol, Italy. The objective of the breeding program is to create new vigorous and freely branching *Portulaca* plants with numerous unique and attractive flowers.

The new *Portulaca* plant is a naturally-occurring branch mutation of *Portulaca umbraticola* Kunth 'Duna Yellow Star', not patented. The new *Portulaca* plant was discovered and selected by the Inventor on a single flowering plant from within a population of plants of 'Duna Yellow Star' in a controlled greenhouse environment in Merano, South Tyrol, Italy during the spring of 2014.

Asexual reproduction of the new *Portulaca* plant by terminal cuttings in a controlled greenhouse environment in Merano, South Tyrol, Italy since the spring of 2014, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LAZPRT1607'. These characteristics in combination distinguish 'LAZPRT1607' as a new and distinct *Portulaca* plant:

1. Outwardly spreading to creeping growth habit.
2. Vigorous growth habit.
3. Freely branching habit.
4. Freely flowering habit.
5. Bright yellow and white-colored flowers.
6. Excellent garden performance.

Plants of the new *Portulaca* can be compared to plants of the mutation parent, 'Duna Yellow Star'. Plants of the new *Portulaca* differ primarily from plants of 'Duna Yellow Star' in flower color as plants of 'Duna Yellow Star' have a less intense (lower contrast) flower color pattern that is unstable. In addition, plants of the new *Portulaca* are more freely branching than plants of 'Duna Yellow Star'.

Plants of the new *Portulaca* can be compared to plants of *Portulaca oleracea* 'Duet Rose Improved', (U.S. Plant Pat. No. 16,152). In side-by-side comparisons, plants of the new *Portulaca* differ primarily from plants of 'Duet Rose Improved' in the following characteristics:

1. Plants of the new *Portulaca* are more compact than plants of 'Duet Rose Improved'.
2. Plants of the new *Portulaca* are more creeping than and not as upright as plants of 'Duet Rose Improved'.
3. Plants of the new *Portulaca* have larger flowers than plants of 'Duet Rose Improved'.
4. Plants of the new *Portulaca* and 'Duet Rose Improved' differ in petal color as plants of 'Duet Rose Improved' have yellow-colored petals with purple-colored centers.

BRIEF DESCRIPTION OF THE PHOTOGRAPHS

The accompanying colored photographs illustrate the overall appearance of the new *Portulaca* plant showing the colors as true as it is reasonably possible to obtain in colored reproductions of this type. Colors in the photographs may differ slightly from the color values cited in the detailed botanical description which accurately describe the colors of the new *Portulaca* plant.

The photograph on the first sheet is a top perspective view of a typical flowering plant of 'LAZPRT1607' grown in a container.

The photograph on the second sheet is a close-up view of a typical flowering plant of 'LAZPRT1607'.

DETAILED BOTANICAL DESCRIPTION

The aforementioned photographs and following observations, measurements and values describe plants grown in 13-cm containers during the spring and summer in an outdoor nursery in Merano, South Tyrol, Italy and under cultural practices typical of commercial *Portulaca* production. During the production of the plants, day and night temperatures ranged from 13.8° C. to 28.6° C. and light levels ranged from 60 to 70 klux. Plants were four months old when the photographs and the description were taken. In the description, color references are made to The Royal Horticultural Society Colour Chart, 1995 Edition, except where general terms of ordinary dictionary significance are used.

Botanical classification: *Portulaca umbraticola* Kunth 'LAZPRT1607'.

Parentage: Naturally-occurring branch mutation of *Portulaca umbraticola* Kunth 'Duna Yellow Star', not patented.

Propagation:

*Type*.—By terminal cuttings.

*Time to initiate roots, summer*.—About 10 days at temperatures about 22° C.

*Time to initiate roots, winter*.—About 14 days at temperatures about 22° C.

*Time to produce a rooted young plant, summer*.—About 24 days at temperatures about 22° C.

*Time to produce a rooted young plant, winter*.—About 28 days at temperatures about 15° C.

*Root description*.—Fine, fibrous; typically pale creamy white in color, actual color of the roots is dependent on substrate composition, water quality, fertilizers, substrate temperature and age of roots.

*Rooting habit*.—Freely branching; medium density.

Plant description:

*Plant and growth habit*.—Spreading to creeping plant habit; vigorous growth habit; relatively rapid growth rate.

*Branching habit*.—Freely branching habit with lateral branches developing at every node; pinching is not required.

*Overall plant height*.—About 15 cm.

*Plant diameter* (*area of spread*).—About 40 cm.

Lateral branch description:

*Length*.—About 30 cm to 50 cm.

*Diameter*.—About 3 mm to 4 mm.

*Internode length*.—About 2 mm to 20 mm.

*Strength*.—Moderately strong.

*Texture*.—Smooth, glabrous; succulent.

*Color*.—Close to 148A underlain with close to 185B.

Leaf description:

*Arrangement*.—Alternate; simple.

*Length*.—About 1.6 cm to 2.2 cm.

*Width*.—About 9 mm to 12 mm.

*Shape*.—Obovate.

*Apex*.—Initially slightly acute becoming more rounded with development.

*Base*.—Obtuse.

*Margin*.—Entire.

*Texture, upper and lower surfaces*.—Smooth, glabrous; succulent.

*Venation pattern*.—Pinnate.

*Color*.—Developing leaves, upper surface: Close to 137A. Developing leaves, lower surface: Close to 147B. Fully expanded leaves, upper surface: Close to 147A; when exposed to full sunlight, margins become closer to 185B in color; venation, close to 147B. Fully expanded leaves, lower surface: Close to 147B; venation, close to 147B.

*Petioles*.—Length: About 1 mm to 2 mm. Diameter: About 1 mm to 2 mm. Texture, upper and lower surfaces: Smooth, glabrous; succulent. Color, upper and lower surfaces: Close to 146C.

Flower description:

*Flowering habit and arrangement*.—Single rotate flowers clustered in terminal cymes; freely flowering habit with potentially about 15 to 30 flowers developing per inflorescence; flowers face mostly upright; flowers sessile.

*Fragrance*.—None detected.

*Natural flowering season*.—Plants begin flowering about six to eight weeks after planting; in the garden, plants flower recurrently from mid-spring to mid-autumn in Italy.

*Flower longevity*.—Flowers last about three days on the plant; flowers not persistent.

*Inflorescence diameter*.—About 5 cm.

*Inflorescence height*.—About 2 cm to 3 cm.

*Flower diameter*.—About 4 cm to 5 cm.

*Flower length* (*height*).—About 1.5 cm to 2 cm.

*Flower buds*.—Length: About 1.2 cm. Diameter: About 5 mm to 7 mm. Shape: Ovoid. Color: Close to 146A to 146B.

*Petals*.—Quantity and arrangement: Five petals in a single whorl. Length: About 2.2 cm. Width: About 1.8 cm. Shape: Obovate. Apex: Cordate. Base: Truncate. Margin: Entire; towards the apex, slightly serrate. Texture, upper and lower surfaces: Smooth, glabrous. Color: When opening and fully opened, upper surface: Close to between 9D and 155C and close to between 13A and 14A; after anthesis, colors become closer to 17A to 17C. When opening and fully opened, lower surface: Close to between 9D and 155C and close to between 12A and 13A; after anthesis, colors become closer to 17A to 17C.

*Sepals*.—Quantity and arrangement: Two, opposite. Length: About 1 cm. Width: About 9 mm. Shape: Deltoid. Apex: Acute. Base: Truncate. Margin: Entire. Texture, upper surface: Smooth, glabrous. Texture, lower surface: Smooth, glabrous; leathery. Color, upper surface: Close to 147C. Color, lower surface: Close to 146A to 146B.

*Reproductive organs*.—Stamens: Quantity per flower: About 50 to 60. Filament length: About 5 mm to 6 mm. Anther shape: Elliptic. Anther length: About 1 mm. Anther color: Close to 24A. Pollen amount: Moderate. Pollen color: Close to 23A. Pistils: Quantity per flower: One. Pistil length: About 1 cm. Style length: About 1 cm.

*Fruits*.—Length: About 4 mm. Diameter: About 6 mm. Texture: Succulent to leathery.

*Seeds*.—Quantity per flower: About 40. Diameter: About 1 mm. Color: Greyish black.

Garden performance: Plants of the new *Portulaca* have been observed to have excellent garden performance and to tolerate rain, wind, drought, heat and low temperatures about 10° C.

Pathogen & pest resistance: Plants of the new *Portulaca* have not been observed to be resistant to pathogens and pests common to *Portulaca* plants.

It is claimed:

1. A new and distinct *Portulaca* plant named 'LAZPRT1607' as illustrated and described.

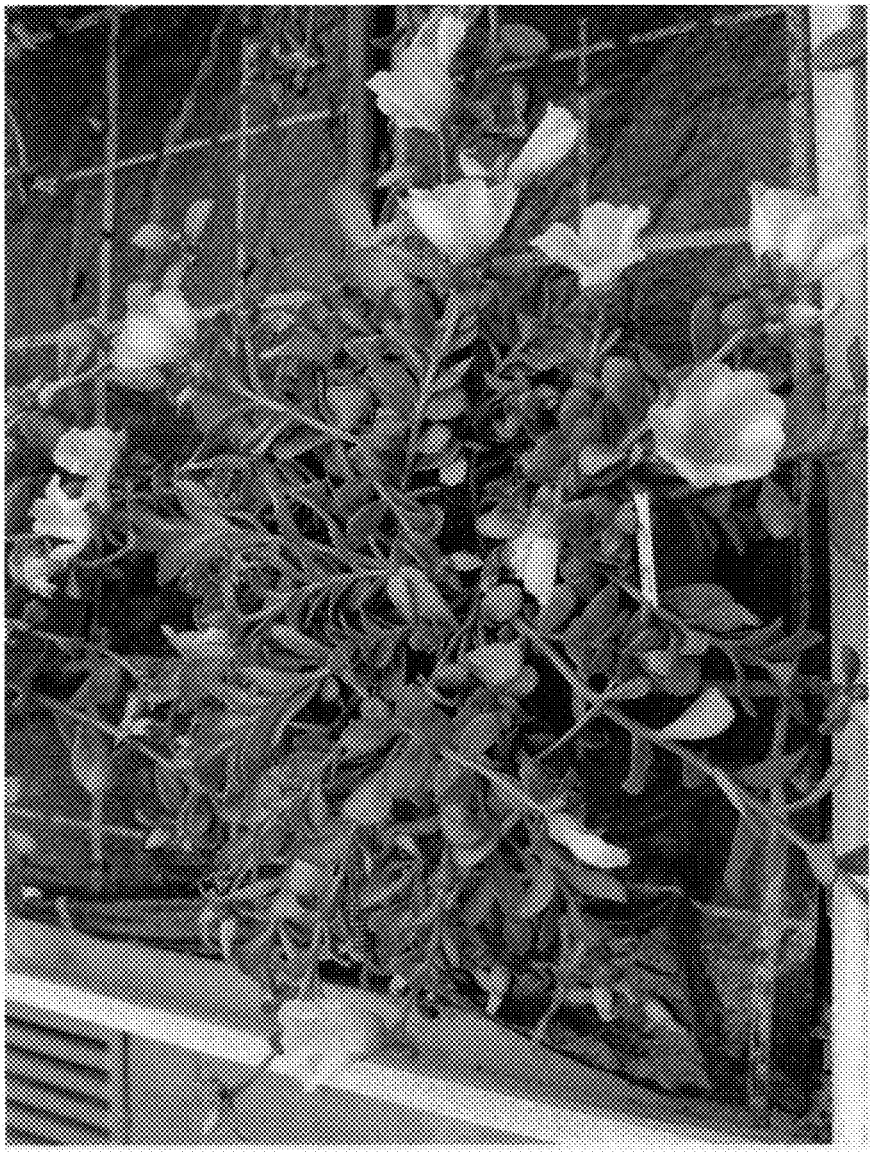

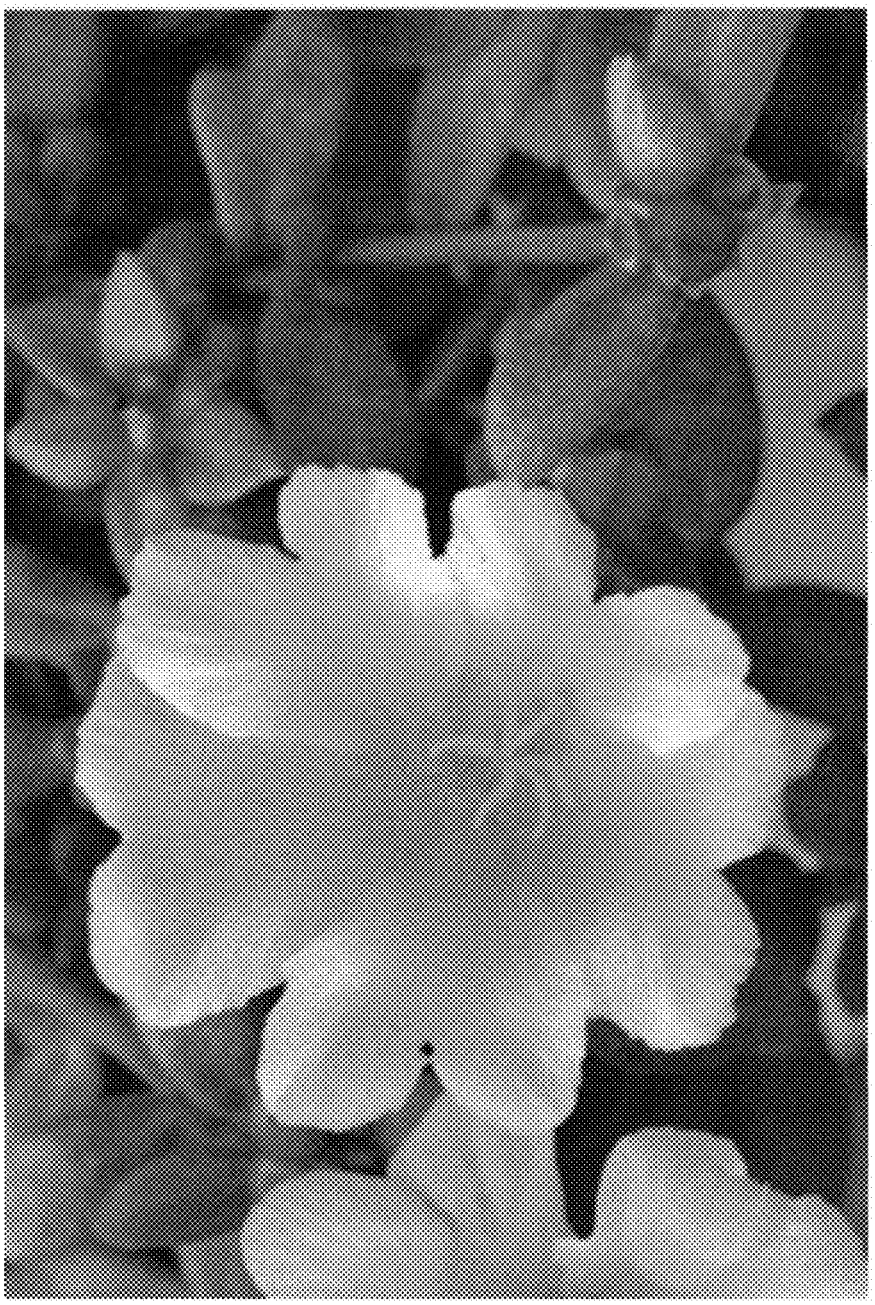

* * * * *